United States Patent
Luecke et al.

(10) Patent No.: US 7,997,797 B2
(45) Date of Patent: *Aug. 16, 2011

(54) COMPUTED TOMOGRAPHY ROTOR RIGIDIFIED BY A METAL MATRIX MATERIAL

(75) Inventors: Daniela Luecke, Germering (DE); Hans-Juergen Mueller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 83 days.

This patent is subject to a terminal disclaimer.

(21) Appl. No.: 12/533,213

(22) Filed: Jul. 31, 2009

(65) Prior Publication Data

US 2010/0027758 A1   Feb. 4, 2010

(30) Foreign Application Priority Data

Aug. 1, 2008   (DE) .................. 10 2008 036 019

(51) Int. Cl.
*H05G 1/02* (2006.01)
*H05G 1/00* (2006.01)
(52) U.S. Cl. ........................................ 378/197; 378/15
(58) Field of Classification Search ................ 378/1, 15, 378/19, 193, 156, 197
See application file for complete search history.

(56) References Cited

U.S. PATENT DOCUMENTS

| 7,447,294 | B2 * | 11/2008 | Sadotomo et al. ............... 378/4 |
| 2006/0018437 | A1 | 1/2006 | Russinger | |
| 2007/0064863 | A1 | 3/2007 | Buttner et al. | |

FOREIGN PATENT DOCUMENTS

| DE | 42 14 858 C1 | 2/1994 |
| DE | 20 2006 004 118 U1 | 8/2007 |

OTHER PUBLICATIONS

U.S. Appl. No. 12/533,228, filed Jul. 31, 2009.
U.S. Appl. No. 12/533,198, filed Jul. 31, 2009.
U.S. Appl. No. 12/533,184, filed Jul. 31, 2009.
U.S. Appl. No. 12/533,148, filed Jul. 31, 2009.

* cited by examiner

*Primary Examiner* — Irakli Kiknadze
(74) *Attorney, Agent, or Firm* — Schiff Hardin LLP

(57) ABSTRACT

A computed tomography apparatus according to the invention ha a rotor that is produced at least in segments from a composite material with metal matrix reinforced with particles. Composite materials with a polymer matrix reinforced with particles have high specific strength properties and rigidity properties with simultaneously low material usage, such that high rotation speeds of the rotor can be achieved without negatively affecting the image quality in generated tomographical images.

8 Claims, 2 Drawing Sheets

COMPUTED TOMOGRAPHY ROTOR RIGIDIFIED BY A METAL MATRIX MATERIAL

BACKGROUND OF THE INVENTION

1. Related Application

The subject matter of the present application is related to the subject matter of an application filed simultaneously with the present application, having 12/533,198, entitled Rigid Computed Tomography Rotor and Method For The Manufacture Thereof.

2. Field of the Invention

The present invention concerns a rotor for a gantry of a computed tomography apparatus, as well as a manufacturing method for such a rotor.

3. Description of the Prior Art

Computed tomography apparatuses enable the reconstruction of three-dimensional slice or volume images of an examination region for diagnostic purposes. The reconstruction of an image ensues on the basis of projections of an examination region that are acquired by irradiating a subject with an x-ray fan beam from different projection directions by rotation of an acquisition device so that measurement data are acquired for parallel projections in an angle range of at least 180 degrees plus the fan angle for reconstruction of an image. To achieve the rotation of the data acquisition device, the computed tomography apparatus has a gantry that has a stationary frame and a rotor arranged such that it can rotate by means of a rotating bearing device. The image data acquisition device is mounted on the rotor. The rotor has been produced conventionally as a cast part made of an aluminum alloy AlZn10SiMg and has a rotor wall in the form of an annular disc and a retention ring running along its outer periphery for mounting the components of the acquisition device. The wall thicknesses of such rotors vary between 15 and 20 mm.

To avoid movement artifacts in the reconstructed image that can arise due to patient or organ movements, it is sought to select the time window for acquisition of the projections required for reconstruction to be as small as possible by the use of high rotation speeds. Rotation speeds of 210 R/min are achieved in current computed tomography apparatuses. In the future the rotation speeds are expected to be increased to at least 300 R/min.

Due to a combination of high rotation speed, large rotation radius and high rotation mass, the rotor represents a highly mechanically stressed component that, in addition to accommodating the stresses that are incurred, must also reliably maintain the positions of x-ray tubes and detectors, since position shifts of the components of more than 0.15 mm can lead to a significant degradation of the image quality.

Significant primary requirements for the rotor of a gantry are accordingly not only a high strength to transfer the forces, but also a high rigidity in order to keep deformations of the rotor (and thus the position shifts of the components of the acquisition device) below the allowable limits, given a simultaneously low weight.

An additional thickening of the existing design would be necessary in order to achieve rotation speeds of 300 R/min and more while keeping the same material. The consequence would be a weight increase of the rotor. Components to drive the rotor and the stationary part of the gantry would thereby also have to be adapted to the greater weight. This approach also has the disadvantage of causing a weight and volume increase of the entire gantry.

SUMMARY OF THE INVENTION

An object of the present invention to provide a computed tomography apparatus and a rotor for a gantry of a computed tomography apparatus so that high rotor rotation speeds can be realized without negatively affecting the image quality in a generated tomographical image.

According to the invention, the rotor for a gantry of a computed tomography apparatus is characterized by the rotor being fabricated, at least in segments, of a particle-reinforced composite material with a metal matrix.

Particle-reinforced composite materials with polymer matrix have high specific strength properties and rigidity properties. Deformation of the rotor is significantly decreased in comparison to a massive rotor produced from an aluminum alloy, even at high rotation speeds of 300 R/min given a simultaneously low weight and small structural volume. The deformation limits to achieve a sufficiently good image quality are not exceeded, even at high rotation speeds.

The costs for transport are reduced due to the achieved weight savings which occurs in that the required rigidity and strength of the rotor is already achieved with a lower material usage in comparison to a massive construction. Moreover, the drive of the rotor can also be dimensioned smaller due to the lower rotation mass, which likewise leads to a cost savings.

The particles are advantageously produced from silicon carbide or from an aluminum alloy. Particularly high strength and rigidity values for the rotor can be achieved via a reinforcement with such particles. The total weight of the rotor is particularly low when the metal matrix is formed from aluminum or an aluminum alloy. The matrix can naturally also be formed with other light metals, for example with magnesium or the like.

In an embodiment of the invention, the rotor has fastening segments without particles. Such fastening segments serve for the attachment of components (for example of components of an acquisition device) to the rotor. In particular, a machine processing in these segments can be achieved in a simple manner so that, for example, interior threads to accommodate threaded bolts can be milled.

In another embodiment of the invention, the distribution density of the particles and/or the particle size can be locally adapted to stress values that arise upon rotation of the rotor. The fact that the mechanical load of the rotor has different local severities, and that the reinforcement must be locally adapted corresponding to this load, is taken into account in this way. In regions of high mechanical load, larger particles should accordingly be used and/or high densities of the particles should be used.

A volume occupied by the particles is advantageously in a range between 105 and 20% of the total volume of the rotor, since sufficiently high rigidity and strength values can be achieved in the range and a manufacture of the composite material is possible with little effort.

DESCRIPTION OF THE PREFERRED EMBODIMENTS

Figure 1:
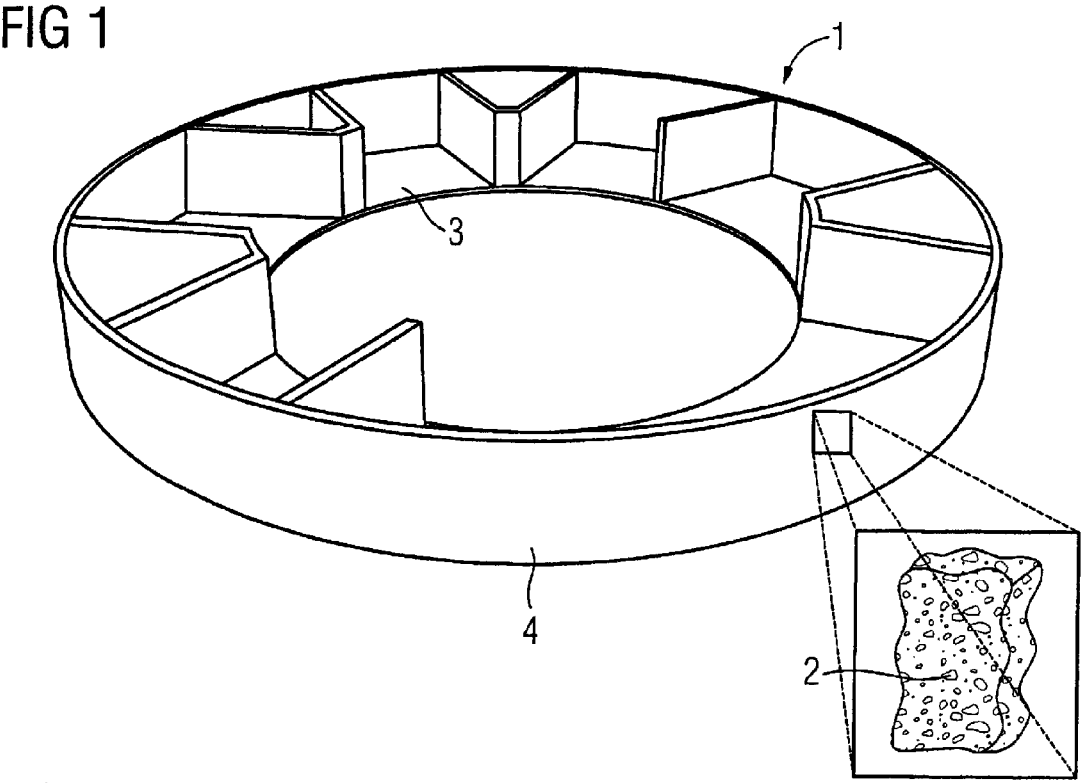
FIG. 1 is a perspective view of a rotor for a gantry of a computed tomography apparatus manufactured from a composite material with particles, with a retention ring arranged running on the outer circumference of a rotor wall.

A rotor 1 according to the invention for a gantry of a computed tomography apparatus is shown in perspective in FIG. 1. The rotor 1 has a rotor wall 3 in the form of a ring rim and a retention ring 4 running on the outer circumference of said rotor wall 3 for the mounting of components of an acquisition device. To increase the rigidity, the rotor 1 has ribs that are connected both with the rotor wall 3 and with the retention ring 4 and thus as connection elements contribute to the increase of the rigidity and strength of the rotor 1. The ribs 5 enable a transfer of forces arising upon rotation of the rotor 1. Via the introduction of such ribs 5, the path of the force flow is reduced in this way, whereby the deformation of the rotor 1 upon rotation is decreased. The rotor 1 also has a rotation bearing device (not shown in this exemplary embodiment) is arranged on the inner circumference of the rotor wall 3. The rotation bearing device interacts with corresponding components of a rotation bearing device on a stationary part of the gantry so that the rotor 1 is mounted so that it can rotate. Components of the image data acquisition device are among the components that are mounted on the rotor 1, but also components of a cooling device of the rotor 1. Components of the acquisition device are, for example, an x-ray radiator and a detector.

To increase the rigidity and strength of the rotor 1 or to reduce the weight with unchanged rigidity and unchanged strength in comparison to a massive design, the rotor according to the invention is produced at least in segments from a composite material with metal matrix reinforced with particles 2. In FIG. 1, a small section of the rotor 1 is shown enlarged in the region of the retention ring 4 as an example, in which region the particle-reinforced composite material is shown. The particles 2 are advantageously produced from silicon carbide or from an aluminum alloy. A particularly high strength and rigidity can be achieved by the use of such particles 2. The metal matrix is advantageously formed of aluminum or an aluminum alloy. This is a light metal with which the total weight of the rotor can be reduced to a significant degree.

The rotor can have fastening segments that contain no particles 2 so that simple machine processing of those segments is possible. Fastening structures (for example threaded bores) are normally introduced into these segments, via which fastening structures the components (for example those of the acquisition device) are attached.

The distribution densities of the particles in the rotor 1 and/or the size of the particles 2 that are used are respectively adapted to the locally present stress values that arise upon rotation of the rotor 1. The distribution densities and the particle size are thereby designed corresponding to the maximum occurring stress values, thus at the highest rotor rotation speed that can be set in operation of the computed tomography apparatus.

The volume occupied by the particles 2 advantageously amounts to between 10% and 20% of the total volume of the rotor 1. Such a mixture ratio between the particles 2 and the matrix leads to a high rigidity and strength of the entire rotor structure.

The rotor 1 shown in this exemplary embodiment is produced from a composite material in which a cast aluminum alloy forms the matrix and in which particles 2 are used that are produced from silicon carbide. Silicon carbide has a higher density than aluminum. However, since the proportion in the composite material is lower, the total density of the rotor increases only minimally. A 20% silicon carbide reinforcement leads to up to a 26% greater rigidity of the rotor 1 in comparison to an unreinforced cast aluminum alloy (AlZn10Si8Mg). Moreover, a composite material reinforced with silicon carbide can be achieved with a weight savings of up to 26% in comparison to the cast aluminum alloy just mentioned. In comparison to gravity casting, better characteristics with regard to the rigidity can be achieved via the more uniform distribution of the particles 2 with a die casting method. However, it would likewise be conceivable that a metal alloy AlSi10CuMnNi is used as a matrix. Given a 20% proportion of particles 2 made of silicon carbide, a weight reduction of up to 36% can be achieved relative to an AlZn10Si8Mg alloy.

The effect of the particle reinforcement can be further improved via subsequent extrusion. For this, input stock made up of a wrought aluminum alloy matrix is reinforced with silicon carbide via either pyrometallurgy or powder metallurgy. The production via powder metallurgy has the advantage that the distribution of the particles 2 is more homogeneous than given production by pyrometallurgy. A particle content of greater than 20% is also additionally possible given composite materials made of a powder material. For the input stock EN-AW6061-T6 produced via pyrometallurgy, an increase in the rigidity of up to 16% can be realized via up to 20% particle reinforcement. Given input stock produced by pyrometallurgy, increases of the specific rigidity of over 144% can be realized for the same alloy via a 20% silicon carbide reinforcement. This percentage can be increased up to 162% via an addition of 30% silicon carbide. A weight reduction of up to 37% can be achieved in comparison to the metal alloy AlZn10Si8Mg.

If the rotation bearing is executed as a cast part, it can be completely reinforced via the addition of particles 2. For this the particles 2 are added into the molten metal to increase the strength and the material rigidity. An agglomeration of the particles is triggered by stirring. The molten mass can subsequently be directly cast. Post processing steps as for the unreinforced rotation bearing are conducted after the cooling.

Figure 2:
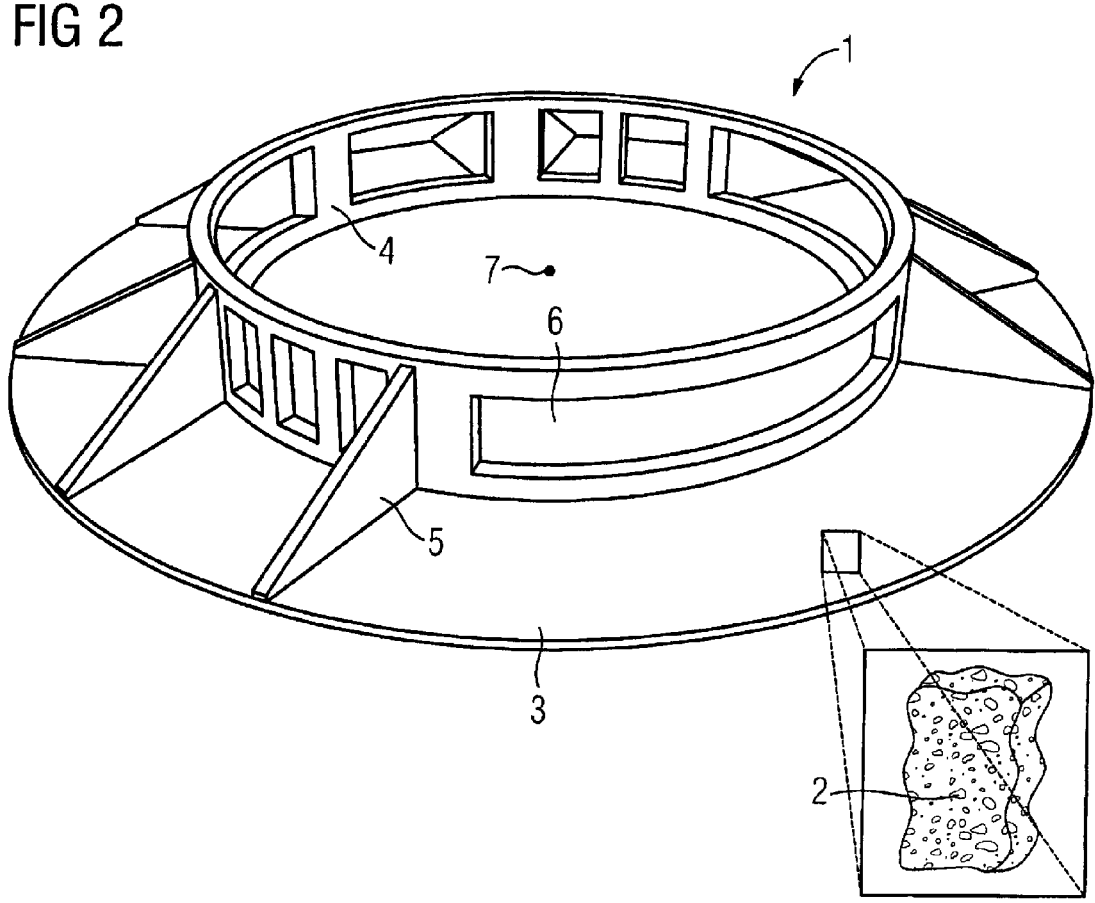
FIG. 2 is a perspective view of a rotor which—in contrast to the rotor shown in FIG. 1—has a retention ring running on the inner circumference of the rotor wall.

A rotor 1 according to the invention is shown in FIG. 2, which differs from the exemplary embodiment shown in FIG. 1 in that the retention ring 4 is arranged on the inner circumference of the rotor wall 3, rather than on the outer circumference of the rotor wall 3, in a perspective view. In a rotor 1 shown in this exemplary embodiment, the rotation bearing device is arranged on the inside of the retention ring 4 (not shown here in further detail). Moreover, the retention ring 4 has recesses 6 that are dimensioned so that components can be inserted in a radial direction traveling away from the rotation center 7 of the rotor 1 and can be positively connected with the rotor 1 via an abutment structure provided at the component. The positive fit thus acts in the direction of centrifugal forces arising upon rotation. In the simplest case, the abutment structure at the component can be a flange that projects from the contour of the component.

In the inserted state, this flange rests directly around the recess 6 in the edge region of the rotor 1. In this case the forces acting on the positive fit distribute over an expanded area so that locally only small stress values occur in the region of the positive connection. This reduces the risk of an ejection of the component. An additional measure that prevents detaching parts or components from being ejected from the region of the rotor 1 thus can be omitted.

Due to the arrangement of the retention ring 4 on the inner circumference of the rotor wall 3, the centrifugal forces arising upon rotation are passed into the rotation bearing device due to the components mounted near the bearing on the rotor 1. The path of the force flow is thereby decreased. A deformation of the rotor 1 that would lead to a degradation of the image quality in the tomographical images to be generated is prevented via the direct transfer of the forces into the rotation bearing device. The composite material reinforced with particles 2 that is used to manufacture such a rotor 1 is dimensioned depending on the locally occurring stress values. Moreover, the mixture ratio between the particles 2 and the metal matrix can be locally adapted depending on the locally present stress values. High stress values are to be expected in the region of the rotor 1 around the recess 6, for example. For this reason it would be suggested to use a higher proportion of particles 2 for local reinforcement of the structure in this region.

Figure 3:
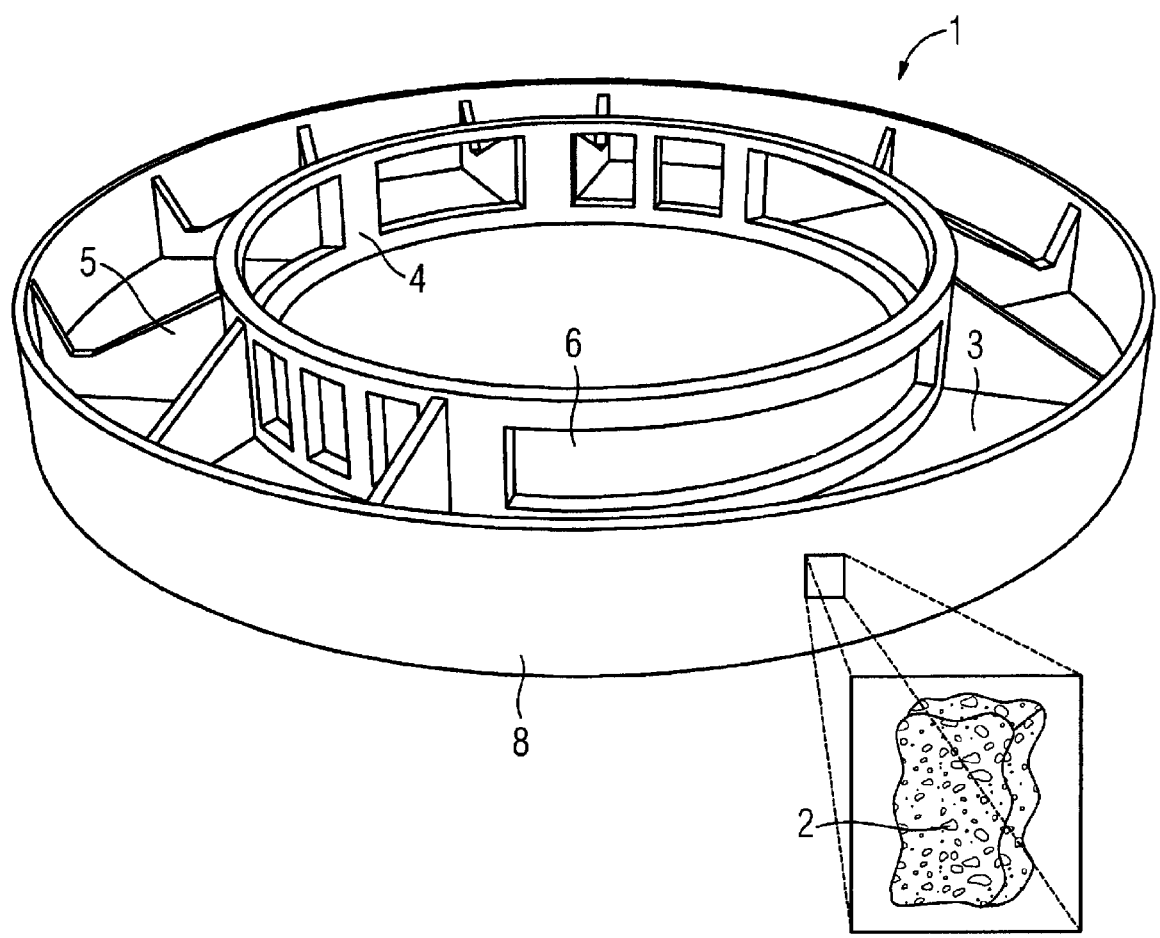
FIG. 3 is a perspective view of the rotor from FIG. 2 with an additional protective ring arranged running on the outer circumference of the rotor wall.

FIG. 3 shows in a perspective view the rotor 1 from FIG. 2 with additional protective ring 9 arranged running on the outer circumference. The protective ring 8 is arranged so that detaching components are caught by the protective ring 8. It is thus prevented that components are ejected, even given failure of the fixed connection between rotor 1 and component. The ribs are connected with the rotor wall 3, the retention ring 4 and the protective ring 8 to stabilize the rotor structure.

In summary, the computed tomography apparatus according to the invention and the rotor 1 according to the invention are characterized by the rotor being produced at least in segments from a composite material with metal matrix reinforced with particles 2. Composite materials with a polymer matrix reinforced with particles 2 have high specific strength properties and rigidity properties with simultaneously low material usage, such that high rotation speeds of the rotor 1 can be achieved without negatively affecting the image quality in generated tomographical images.

Although modifications and changes may be suggested by those skilled in the art, it is the intention of the inventors to embody within the patent warranted hereon all changes and modifications as reasonably and properly come within the scope of their contribution to the art.

We claim as our invention:

1. A rotor for a computed tomography gantry, comprising:
   a rotor structure having a configuration to mount image data acquisition components of a computed tomography apparatus thereon, said rotor structure also being configured for rotation around a rotation center and said rotor structure being subject to force stresses therein that occur due to rotation of said rotor structure; and
   said rotor structure being comprised, at least in segments of said rotor structure, of a composite material having a metal matrix reinforced with particles, said particles having a particle size that is locally adapted to said force stresses.

2. A rotor as claimed in claim 1 wherein at least some of said particles are comprised of silicon carbide.

3. A rotor as claimed in claim 1 wherein least some of said particles are comprised of an aluminum alloy.

4. A rotor as claimed in claim 1 wherein said metal matrix is comprised of a metal selected from the group consisting of aluminum and aluminum alloys.

5. A rotor as claimed in claim 1 wherein said rotor structure comprises at least some segments that are not reinforced with said particles, said at least some segments being configured for mounting said image data acquisition components thereon.

6. A rotor as claimed in claim 1 wherein said rotor structure is subject to force stresses therein that occur due to rotation of said rotor structure, and wherein said particles are distributed in said rotor structure with a distribution density adapted to said force stresses.

7. A rotor as claimed in claim 1 wherein said particles occupy a volume in said rotor structure in a range between 10% and 20% of a total volume of said rotor structure.

8. A computed tomography gantry comprising:
   a stationary frame;
   a computed tomography image data acquisition system comprising a plurality of image data acquisition components;
   a rotor mounted for rotation in said stationary frame, said plurality of image data acquisition components being mounted on said rotor for co-rotation with said rotor around a rotation center; and
   said rotor comprising a rotor structure to which said plurality of image data acquisition components are mounted, said rotor structure being subject to force stresses therein that occur due to rotation of said rotor structure, said rotor structure being comprised, at least in segments of said rotor structure, of a composite material having a metal matrix reinforced with particles, said particles having a particle size that is locally adapted to said force stresses.

* * * * *